United States Patent [19]
Wishman

[11] 4,381,611
[45] May 3, 1983

[54] METHOD AND APPARATUS FOR ABSORBING MOISTURE

[75] Inventor: Marvin Wishman, Greenville, S.C.

[73] Assignee: Phillips Petroleum Company, Bartlesville, Okla.

[21] Appl. No.: 260,472

[22] Filed: May 4, 1981

Related U.S. Application Data

[62] Division of Ser. No. 844,350, Oct. 21, 1977, abandoned.

[51] Int. Cl.³ .............................................. F26B 5/16
[52] U.S. Cl. ............................................. 34/9; 34/95; 128/156; 428/284; 604/312
[58] Field of Search ............... 34/95, 9; 128/284, 287, 128/155, 156, 296; 156/148; 428/235, 284

[56] References Cited

U.S. PATENT DOCUMENTS

| | | | |
|---|---|---|---|
| 3,545,442 | 12/1970 | Wicker | 156/148 |
| 3,701,164 | 10/1972 | Blore | 2/409 |
| 3,768,480 | 10/1973 | Mesek et al. | 128/287 |
| 3,864,157 | 2/1975 | Bresson et al. | 428/284 |
| 3,881,489 | 5/1975 | Hartwell | 128/287 |
| 3,916,900 | 11/1975 | Breyer et al. | 128/287 |
| 3,949,130 | 4/1976 | Sabee et al. | 128/296 |
| 4,042,655 | 8/1977 | Platt et al. | 156/148 |
| 4,054,141 | 10/1977 | Schwaiger | |

Primary Examiner—Larry I. Schwartz

[57] ABSTRACT

An improved nonwoven polypropylene fabric, having the fibers on one side fused and the fibers on the opposite side unfused, which fabric when wetted exhibits a wet feeling on the fused side and a substantially dry feeling on the unfused side. Also disclosed are bandage, diaper, hat sweatband and headband or wristband structures employing the fabric as well as a method of transferring moisture from a moisture-bearing surface utilizing the fabric.

11 Claims, 7 Drawing Figures

METHOD AND APPARATUS FOR ABSORBING MOISTURE

This is a division of application Ser. No. 844,350, filed Oct. 21, 1977, now abandoned.

This invention relates to nonwoven fabrics. More particularly, this invention relates to method and means for utilizing an improved nonwoven polypropylene fabric.

It is desirable to provide for the removal of moisture in the form of perspiration and the like from the skin of human beings, especially those involved in physical exercise. A common method of removal of such moisture involves the application of moisture-absorbent cloth, such as cotton terry cloth or the like, to the moist skin. The use of headbands and wristbands of moisture-absorbent cloth is common among participants in athletics to keep the perspiration from flowing into the eyes or onto the hands and impairing the vision or grip of the exercising individual. Similarly, hats are commonly provided with sweatbands to absorb perspiration from the head of a hat wearer.

In the instances noted above, the moisture-absorbent headbands, wristbands and hat sweatbands normally maintain the moisture absorbed thereby in contact with the skin of the wearer which, aside from being uncomfortable to the wearer, can restrict normal evaporation of moisture from the contacted skin surface which can cause irritation and promote the development of skin rashes.

It is also desirable to absorb body liquids from infants through the use of diapers. Disposable diapers have been developed which provide a degree of moisture absorption and isolation which is superior to the conventional cloth diaper. However, it is desirable that a disposable diaper be capable of both absorbing body fluids from the perineal region of an infant and isolating such absorbed fluids out of contact with the skin of the infant to keep the area as dry as possible and thus reduce the incidence of skin irritation and rash.

It is further desirable to absorb and isolate body fluids from a sore or a wound to maintain it in as dry a condition as possible to promote rapid healing and reduce the possibility of infection. In the past, the conventional means for accomplishing this task has involved the use of bandages or compresses formed of moisture-absorbent cloth which characteristically maintain the fluid absorbed thereby in contact with the sore or wound thus retarding the evaporative drying of the sore or wound and retarding the healing process.

The present invention provides novel method and means for transferring moisture in the form of perspiration, body fluid or the like from the skin of an individual which overcomes the problems noted above.

I have discovered that a nonwoven fabric, formed of staple polypropylene fibers which have been drawn, needled and fused on a single side thereof, exhibits an unexpected and surprising property characterized in that when such fabric is wetted, water is released through the fused side but is not released through the unfused or beard side. This characteristic or property of such a fabric is so marked that when the wetted fabric is placed against the skin the fabric feels wet on the fused side and dry on the unfused or beard side. More particularly, the fused side of the wetted fabric will wet an object in contact therewith while the unfused or beard side will not wet such an object contacted thereby.

The present invention provides a method of transferring moisture from a moisture-bearing surface by contacting such surface with the unfused or beard side of a nonwoven fabric comprising a plurality of polypropylene fibers which fibers are fused on the opposite side.

The present invention further provides a moisture-absorbing structure employing a nonwoven fabric of polypropylene fibers having a single fused side.

In another embodiment the present invention provides a bandage structure employing a nonwoven fabric of polypropylene fibers having a single fused side in the construction thereof.

In yet another embodiment the present invention provides a multilayer diaper structure employing a nonwoven polypropylene fabric having a single fused side in the construction thereof.

In still another embodiment the present invention provides a sweatband structure for use in a hat.

In still another embodiment the invention provides a sweatband or wristband structure employing a nonwoven polypropylene fabric having a single fused side in the construction thereof.

It is, therefore, an object of the present invention to provide an improved method of removing and transferring liquid from a liquid-bearing surface or the like.

Another object of the invention is to provide improved means for removing and transferring liquid from a liquid-bearing surface.

Other objects and advantages of the present invention will be readily apparent to those skilled in the art from a reading of the following detailed description and claims, together with the accompanying drawings in which:

Figure 1:
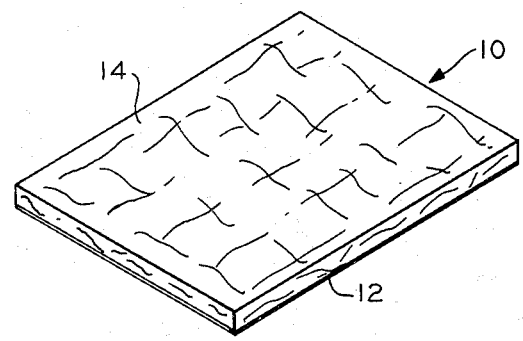
FIG. 1 is a perspective view of a piece of nonwoven fabric as empolyed in the present invention.

Referring now to the drawings, FIG. 1 shows a rectangular piece of nonwoven fabric 10. The nonwoven fabric is preferably produced by the method which comprises forming a batt or web comprising polypropylene fibers oriented primarily in the fill direction, drafting the batt in the warp direction, needling the drafted batt to entangle the fibers drafting the needled batt in both the warp and fill directions, and fusing one side of the resulting batt by suitable means such as infrared radiation. Such a process is disclosed in Platt et al., U.S. Pat. No. 4,042,655, dated Aug. 16, 1977, the text of which is incorporated herein by reference. The fabric 10 is preferably formed of nonwoven, polypropylene fibers in the form of staple or continuous filaments which have been drawn and needled to form a web or batt which is fused on one side 12 thereof. The opposite side 14 of the fabric 10 is unfused and forms a relatively rough or fuzzy beard side of the fabric 10.

When the nonwoven polypropylene fabric, fused on one side and unfused on the opposite side, is wetted, the moisture adsorbed on the unfused or beard side migrates or wicks through the fabric toward the fused side of 12.

Such a polypropylene fabric thus presents a dry or substantially dry surface to the touch on the unfused or beard side 14 and presents a comparatively wet surface to the touch on the fused side 12. Thus, the fabric 10, when suitably sterilized, provides an adsorbent means or structure suitable for a bandage or bandage pad or compress which, when placed over a moisture-bearing surface, such as a wound, serves to transmit moisture such as body fluids contacted by the unfused beard side 14 of the fabric 10 away from the moisture-bearing surface to the fused side 12 of the fabric.

Figure 2:
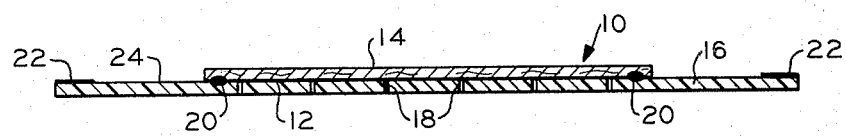
FIG. 2 is a partial, cross-sectional view of a moisture-absorbent bandage assembly constructed in accordance with the present invention.

As shown in FIG. 2 there is illustrated in cross-section a bandage structure or the like wherein the fabric 10 is secured or adhered by suitable means to a backing strip 16 with the fused side 12 proximate to the backing strip 16 and with the unfused side 14 directed away from the backing strip. The backing strip 16 can suitably be constructed of a moisture-impervious sheet or the like which may be suitably constructed of a flexible plastic material such as polyethylene or polypropylene. Such structure can also be advantageously employed as a diaper with the unfused side of the fabric 10 in contact with the wearer.

The backing strip 16 can, if desired, be provided with perforations 18 therein adjacent to the fused side 12 of the fabric to permit moisture accumulating on the fused side to evaporate. The fabric 10 can be secured to the backing strip 16 by a suitable cement, or may be fused thereto as shown at 20. The backing strip can be provided with a suitable adhesive 22 on the surface 24 thereof for securing the fabric 10 in a desired position relative to a moisture-bearing surface.

Figure 3:
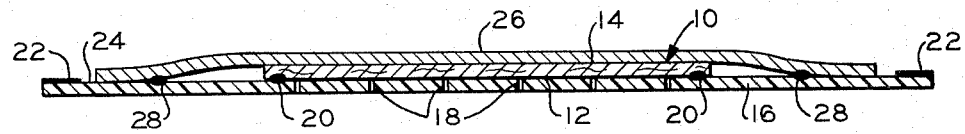
FIG. 3 is a partial, cross-sectional view similar to FIG. 2 showing another form of moisture-absorbent bandage assembly.

FIG. 3 illustrates a structure slightly modified from that illustrated in FIG. 2 wherein a moisture-pervious sheet 26 is positioned over the unfused side 14 of the fabric 10 to provide a moisture-pervious barrier between the fabric 10 and a moisture-bearing surface, such as a wound, which barrier prevents the fabric from sticking to the wound. The backing strip 16 can again be provided with perforations 18 therein if desired. The sheet 26 can be suitably secured to the backing strip 16 by means of adhesive or the like as shown at 28.

Figure 4:
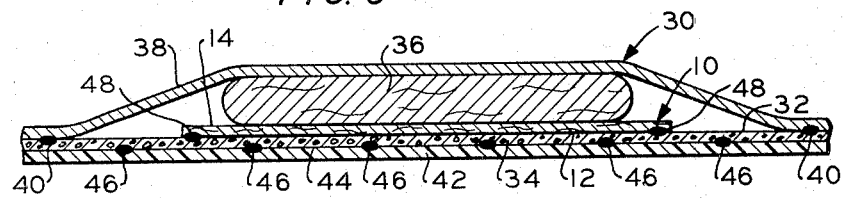
FIG. 4 is a partial, cross-sectional view showing one form of moisture-absorbent diaper assembly constructed in accordance with the present invention.

Referring now to FIG. 4, a disposable diaper 30 is illustrated in cross-section. The construction of the diaper 30 is characterized by the employment of a suitably dimensioned piece of nonwoven fabric 10 wherein the fused side 12 thereof is disposed in contact with the upper surface 32 of a resilient foam layer 34, which foam layer is preferably of cellular construction having elastomeric and wet-stable properties to facilitate the conformation of the diaper about the legs and body of a wearer. The foam layer 34 can be either hydrophilic or hydrophobic. The unfused side 14 of the nonwoven fabric 10 is in contact with a suitable moisture-absorbent core or batt 36 which may be suitably constructed of a loosely compacted assemblage of cellulosic fibers. A moisture-pervious facing sheet or layer 38 is positioned over the batt 36 and piece of nonwoven fabric 10 and is secured to the upper surface 32 of the foam layer 34 by suitable means such as an adhesive as shown at 40. A moisture-impervious backing sheet 42 is disposed adjacent the lower surface 44 of the foam layer 34 and is preferably secured thereto by suitable means such as through the use of a suitable adhesive as shown at 46. The backing sheet 42 can be suitably formed of a relatively thin sheet of flexible plastic such as polyethylene or polypropylene.

The multilayer, disposable diaper 30, when properly positioned on the wearer, readily absorbs moisture through the moisture-pervious facing sheet 38 into the moisture-absorbent core 36, which moisture is then drawn from the core 36 through the novel wicking action of the nonwoven fabric 10, such moisture accumulating along the fused side 12 thereof.

Figure 5:
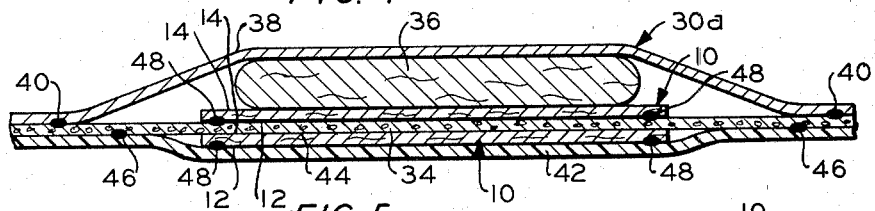
FIG. 5 is a partial, cross-sectional view similar to FIG. 4 showing another form of moisture-absorbent diaper assembly.

FIG. 5 illustrates a slightly modified disposable diaper structure which is designated by the reference character 30a. The diaper 30a differs from the previously described diaper 30 in that a second piece of nonwoven fabric 10 is disposed intermediate the lower surface 44 of the foam layer 34 and the moisture-impervious backing sheet 42, with the fused side 12 of the second piece of fabric 10 adjacent the backing sheet 42 and with the unfused side 14 contacting the foam layer 34.

In both the diapers 30 and 30a, the pieces of nonwoven fabric 10 may be adhered to the foam layer 34 by suitable means such as an adhesive as shown in 48.

Figure 6:
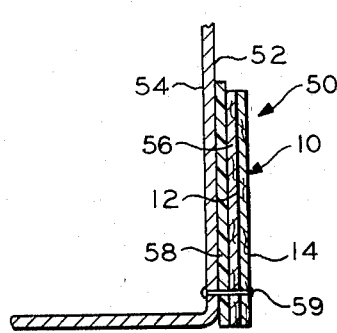
FIG. 6 is a partial, cross-sectional view of a hat and hat sweatband constructed in accordance with the present invention.

FIG. 6 illustrates a hatband or sweatband generally designated by the reference character 50 secured within and around the crown 52 of a hat 54. The sweatband 50 comprises a strip of nonwoven fabric 10, as described above, having the unfused side 14 thereof facing inwardly to engage the head of the wearer of the hat in moisture-conducting relation. The fused side 12 of the fabric strip 10 is disposed adjacent the inner surface of a moisture absorbent strip 56 in moisture conducting relation to facilitate the transfer of moisture to the strip 56. The outer surface of the moisture-absorbent strip 56 is positioned against a substantially moisture-impervious backing sheet or strip 58 which, in turn, contacts the inner surface of the crown 52. The lower edges of the strips 10, 56 and 58 comprising the sweatband 50 are suitably secured about the lower periphery of the crown 52 by suitable means such as stitching as shown at 59.

Figure 7:
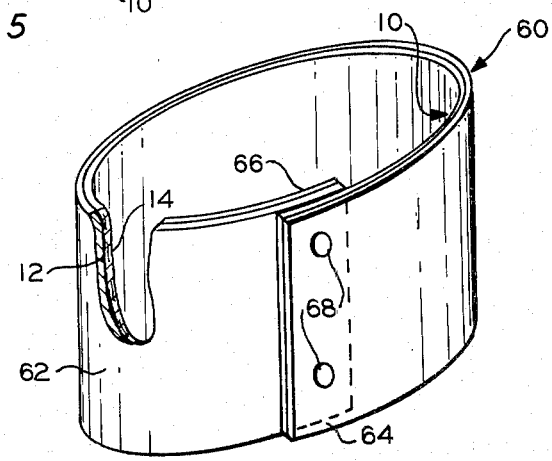
FIG. 7 is a perspective view of a moisture-absorbent headband or the like constructed in accordance with the present invention with a portion thereof broken away to more clearly illustrate details of construction.

FIG. 7 illustrates a novel headband or wristband structure generally designated by the reference character 60. The headband 60 comprises a nonwoven polypropylene fabric strip 10 as described previously. The unfused side 14 of the strip 10 faces inwardly to engage the skin of a wearer in moisture-conducting relation, while the fused side 12 of the strip 10 is disposed in contact with the inner surface of a moisture-absorbent outer strip 62, which can be suitably formed of cotton terry cloth or the like, whereby moisture from the wearer's skin wicks or migrates from the unfused side 14 of the fabric strip 10 to the fused side 12, the moisture then being readily absorbed from the fused side 12 by the moisture-absorbent strip 62. The opposite ends of the headband 64 and 66 are provided with suitable means for securing the band 60 about the head of the wearer or, about the wrist of a wearer. Such suitable means includes conventional friction snaps as shown at 68. Alternately, suitable means for securing the ends 64 and 66 together can be provided by a Velcro hook-and-eye connection or an elastic stretch band.

The newly discovered novel characteristic of the nonwoven polypropylene fabric 10 which renders the previously described structures advantageous for their intended uses, is the capacity of the fabric, when subjected to moisture, to present a substantially dry feeling on the beard or unfused side 14 thereof while the fused side 12 exhibits a substantially wet feeling. This novel characteristic of the nonwoven polypropylene fabric 10 is apparently attributable to the capacity of polypropylene fibers to cause the wicking or migrating of moisture therethrough. However, until now it had not been known that a nonwoven polypropylene fabric having a fused surface on one side and an unfused surface on the opposite side exhibits the previously described wet and dry feeling. It has been found that nonwoven polypropylene fabric which is fused on one side in response to the application of infrared heat thereto exhibits this characteristic in a most pronounced manner. For example, a fabric so constructed, made from polypropylene fibers of 3 denier ×3.25" (8.25 cm) formed into a fabric weighing 3.5 oz/yard (82.6 grams/sq. meter) and fused on one side with infrared heat, exhibited the described characteristics. However, nonwoven polypropylene fabric which is fused on one side through other means such as the application of a heated roll thereto in the formation of the fabric exhibits the same characteristic.

It will be seen in each of the previously described structures in which the nonwoven polypropylene fabric 10 is employed that this unique and newly discovered characteristic of the fabric 10 is advantageously employable in a number of practical applications such as the manufacture of bandage pads or compresses, bandages, disposable diapers, hat sweatbands, headbands, and wristbands, etc. wherein it is advantageous to conduct moisture away from a moisture-bearing surface such as a wound, the perineal region of an infant, the skin and hair of the wearer of a hat and the perspiration laden skin and hair of a perspiring individual, and maintain the moisture separated from the moisture-bearing surface.

Reasonable variations and changes may be made in the construction and arrangement of parts or elements of the various embodiments as disclosed herein without departing from the spirit and scope of the invention as defined in the following claims.

What is claimed is:

1. A method of transferring liquid from a liquid-bearing surface, comprising:

positioning a nonwoven fabric comprising a plurality of staple polypropylene fibers including a plurality of unfused polypropylene fibers on a first side thereof and a second plurality of fused polypropylene fibers on a second opposite side thereof with at least a portion of the unfused fibers of the first side in contact with the liquid on the liquid-bearing surface; and allowing the liquid from the liquid-bearing surface to migrate through the unfused fibers to the fused fibers on the second side of the nonwoven fabric.

2. A method in accordance with claim 1 wherein said polypropylene fibers comprise staple fibers.

3. A method in accordance with claim 1 wherein said polypropylene fibers comprise continuous fibers.

4. A method in accordance with claim 1 wherein said polypropylene fibers are staple fibers.

5. A method in accordance with claim 1 wherein said nonwoven fabric is positioned in contact with the liquid with a moisture-pervious layer interposed between said nonwoven fabric and the liquid-bearing surface.

6. A method in accordance with claim 1 or claim 5 wherein the liquid-bearing surface is the skin of a living being.

7. A method of transferring liquid from a liquid-bearing surface, comprising:

positioning a nonwoven fabric comprising a plurality of polypropylene fibers including a plurality of unfused polypropylene fibers on a first side of said nonwoven fabric and a second plurality of fused polypropylene fibers on a second opposite side of said nonwoven fabric with at least a portion of the unfused fibers of the first side in liquid flow communication with the liquid on the liquid-bearing surface; and allowing the liquid thus communicating with the unfused fibers to migrate through the unfused fibers to the fused fibers on the second side of said nonwoven fabric.

8. A method in accordance with claim 7 wherein a moisture-pervious sheet is interposed between said nonwoven fabric and the liquid-bearing surface prior to the positioning step.

9. A method in accordance with claim 8 wherein a moisture-absorbent core is interposed between said moisture-pervious sheet and the first side of said nonwoven fabric prior to the positioning step.

10. A method in accordance with claim 1 or claim 7 characterized further to include removing liquid from the second side of the nonwoven fabric.

11. A method in accordance with claim 7 wherein said polypropylene fibers are staple fibers.

* * * * *